United States Patent [19]

Suzuki et al.

[11] Patent Number: 5,087,446
[45] Date of Patent: Feb. 11, 1992

[54] SKIN COSMETICS

[75] Inventors: Eriko Suzuki; Jun Hiraki, both of Yokohama; Masahiro Fujii, Ohta, all of Japan

[73] Assignee: Chisso Corporation, Japan

[21] Appl. No.: 472,296

[22] Filed: Jan. 30, 1990

[30] Foreign Application Priority Data

Feb. 15, 1989 [JP] Japan .................................. 1-33791

[51] Int. Cl.$^5$ .............................................. A61K 7/02
[52] U.S. Cl. ............................................. 424/62; 424/63; 424/69; 514/777; 514/785
[58] Field of Search .................. 536/54, 55.1, 55.2, 536/55.3; 424/62, 63, 69; 514/54, 62, 777, 474, 785

[56] References Cited

U.S. PATENT DOCUMENTS 3,396,081 8/1968 Billek ........................... 536/55.1 X
3,767,807 10/1973 Blonde ................................ 514/474

FOREIGN PATENT DOCUMENTS 60-116618 6/1985 Japan ...................................... 514/54
2218429 11/1989 United Kingdom .

Primary Examiner—Thurman K. Page
Assistant Examiner—Susan S. Rucker
Attorney, Agent, or Firm—Leydig, Voit & Mayer

[57] ABSTRACT

The invention provides cosmetics using a freeze-dried material which is obtained by freeze-drying an aqueous solution. The solution contains hyaluronic acid or sodium hyaluronate and magnesium-L-ascrbil phosphate.

7 Claims, No Drawings

SKIN COSMETICS

BACKGROUND OF THE INVENTION

The present invention relates to cosmetics which contain hyaluronic acid or sodium hyaluronate (abbreviated hyaluronic acid (hyaluronate) hereinafter) and a derivative of L-ascorbic acid.

Conventional powder or granular cosmetics are principally used for whitening the skin. As the main materials, water-soluble powder and a stable derivative of ascorbic acid having a skin whitening effect are contained in the cosmetics. For using the cosmetics, the powder or granular cosmetics are applied on the skin after dissolving in water or face lotion on the palm of the hand.

It was expected to obtain excellent cosmetics by combining sodium hyaluronate having moisture retention and the derivatives of ascorbic acid having the skin whitening effect. However, sodium hyaluronate and the derivatives of ascorbic acid have disadvantages because it is difficult to dissolve these compounds in water.

When these conventional powder or granular cosmetics are applied on the skin after attempting to homogeneously dissolve or disperse them in a liquid on the palm of the hand, the cosmetics have the following problems.

1) It is difficult to mix homogeneously the powder in water and it is difficult to dissolve the powder, particularly the powder obtained from ground granules because it floats on water.

2) When these cosmetics are applied, a rough reaction is produced on the skin.

SUMMARY OF THE INVENTION

The present inventors have earnestly strived to solve the above problems and have found that these problems are solved by using a dried material which is obtained by freeze-drying an aqueous solution containing hyaluronic acid (hyaluronate) and magnesium-L-ascorbyl phosphate.

The present invention provides a cosmetic containing a freeze-dried material which is obtained by freeze-drying an aqueous solution, the solution contains hyaluronic acid (hyaluronate) and magnesium-L-ascorbyl phosphate.

DETAILED DESCRIPTION OF THE INVENTION

Hyaluronic acid is found in animal tissue, e.g. in synovial fluid, vitreous humor, umbilical cord, cartilage, skin, rooster combs and it plays an important part in a living body. The above said hyaluronic acid is a high-molecular weight substance. As its solution has a high viscosity, elasticity and water retention, it is widely used as cosmetic materials, ophthalmology medicine, eyewater and arthropathy medicines.

Hitherto, hyaluronic acid (hyaluronate) is industrially produced by extracting from rooster combs, glass bodies of cow's eyes, navel strings and the like, or by incubating micro-organisms having the ability of hyaluronic acid production (a fermentation method). Hyaluronic acid (hyaluronate) used in the present invention can be obtained either by the extraction method or by the fermentation method.

L-Ascorbic acid (Vitamin C) is widely distributed in the vegetable kingdom and the animal kingdom, and particularly it is abundantly contained in green vegetables and fruits. It is known that L-ascorbic acid has various kinds of physiological and pharmacological effects, and particularly in the treatment of pigmentation troubles is known among persons in the cosmetics industry. The most important factor for determining skin colors is melanin. L-Ascorbic acid exerts two effects to melanin as follows.

1) Dopaquinone, which is produced in the initial stage of melanin formation, is reduced by using L-ascorbic acid to DOPA.

2) Melanin is reduced and turns into a light color type.

On one hand, L-ascorbic acid is relatively stable on drying, on the other hand, it has a disadvantage that it is easily oxidized in an aqueous solution in the presence of air and water. Accordingly, derivatives of L-ascorbic acid chracterized in that they have water-solubility and stability in air and water and are easily blended in cosmetics materials have been investigated. As a result, magnesium-L-ascorbyl phosphate represented by the following formula has been prepared as cosmetic for whitening the skin. In the present invention, the above magnesium-L-ascorbyl phosphate is used.

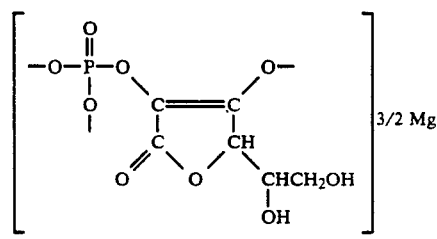

The freeze-drying of the aqueous solution containing hyaluronic acid (hyaluronate) and magnesium-L-ascorbyl phosphate is carried out by the following process as an example.

To a water solution containing 0.05–2.0% by weight of hyaluronic acid (hyaluronate), magnesium-L-ascorbyl phosphate is slowly added with stirring to dissolve thoroughly. Otherwise, hyaluronic acid (hyaluronate) may be added to a water solution containing magnesium-L-ascorbyl phosphate. The mixture of hyaluronic acid (hyaluronate) and magnesium-L-ascorbyl phosphate is freeze-dried to obtain the freeze-dried product of hyaluronic acid (hyaluronate) and magnesium-L-ascorbyl phosphate. The weight ratio of hyaluronic acid (hyaluronate) to magnesium-L-ascorbyl phosphate can be arbitrarily changed. Practically, the weight ratio is preferably 0.1–50 of magnesium-L-ascorbyl phosphate to hyaluronic acid (hyaluronate). When the ratio of hyaluronic acid (hyaluronate) is high, desirably the mixture is pre-frozen before freeze-drying.

When the ratio of hyaluronic acid (hyaluronate) is low, since the freeze-dried product obtained has high rate of moisture adsorption, the vessel containing the product is preferably capped in vacuo.

When the powder of hyaluronic acid (hyaluronate) is dissolved in water, it takes a long time to dissolve the powder because the viscosity of the solution is high and undissolved lumps are formed. Further, it is difficult to dissolve the powder or granules of magnesium-L-ascorbyl phosphate in water. However, the freeze-dried product of the present invention obtained from the water solution containing hyaluronic acid (hyaluronate) and magnesium-L-ascorbyl phosphate is advantageous because it is difficult to form undissolved lumps and it takes a short time to dissolve the product in water, compared with the powder of hyaluronic acid (hyalronate).

Moreover, the freeze-dried product can be dissolved in a short time, compared with the powder or granules of magnesium-L-ascorbic phosphate.

Because of the above advantage, the freeze-dried product used in the present invention containing hyaluronic acid (hyaluronate) and magnesium-L-ascorbyl phosphate can be used as the powder constituent of cosmetic materials comprising face lotion and face powder.

When the freeze-dried material used in the present invention containing hyaluronic acid (hyaluronate) and magnesium-L-ascorbyl phosphate is dissolved by adding water or face lotion on the palm of the hand, the material can be easily dissolved in water or face lotion. Accordingly, when the solution is applied on the skin, no sensation of roughness on the skin is noted. The aqueous solution containing dissolved powder is viscous and it can be applied easily on the skin. As a result, the cosmetics of the present invention can be used by applying the solution obtained by dissolving the powder in water or face lotion on the skin.

Such cosmetics have both the moisture retention of hyaluronic acid (hyaluronate) and the skin whitening effect of magnesium-L-ascorbyl phosphate.

To the powder cosmetics of the present invention, in addition to the above essential constituents, face paints, colors or coloring agents, powder materials, antioxidants, granular material, extenders, perfumery, etc. may be added.

The skin cosmetics containing hyaluronic acid (hyaluronate) and magnesium-L-ascorbyl phosphate which are obtained by the above process have the following merits.

1) There is no lowering of molecular weight of hyaluronic acid (hyaluronate).

2) The freeze-dried material is homogeneously mixed in water and it is difficult to form undissolved lumps.

3) It takes a short time to dissolve the material in water, compared with hyaluronic acid (hyaluronate) alone.

4) It takes a short time to dissolve the material in water, compared with magnesium-L-ascorbyl phosphate.

5) When the water solution containing the material is applied on the skin, it feels smooth rather than rough to the skin.

6) The material has both the moisture retention and the skin whitening effect.

DESCRIPTION OF PREFERRED EMBODIMENTS

The following examples illustrate the present invention more specifically. In these examples, the term % stands for percentage by weight.

EXAMPLE 1

Preparation of the Cosmetic of this Invention

To 100 ml of purified water, 1.0 g of magnesium-L-ascorbyl phosphate was dissolved. To the obtained solution, 0.5 g of sodium hyaluronate (molecular weight: 1,100,000) was added and dissolved. Then, the solution was charged in a short neck Kjeldahl flask having a volume of 1000 ml and previously frozen at −40° C. and freeze-dried at room temperature for 18 hours with a freeze drier (manufactured by Tokyo Rika Company, Type FD-1) at 0.05 torr to obtain 1.1 g of the freeze-dried material. The analytical results are shown in Table 1. The molecular weight was determined with a high speed liquid chromatography.

TABLE 1

|  | Example 1 |
|---|---|
| Magnesium-L-ascorbyl phosphate | 57.3% |
| Sodium hyaluronate | 32.9% |
| Weight loss by drying | 9.8% |
| Molecular weight of sodium hyaluronate | 1,000,000 |
| Viscosity (cps) | 86.9 |
| pH (0.1% water solution) | 7.2 |

EXAMPLE 2

Preparation of the Cosmetic of this Invention

To 200 ml of purified water, 1.0 g of magnesium-L-ascorbyl phosphate was dissolved. To the obtained solution, 0.5 g of sodium hyaluronate (molecular weight 1,200,000) was added and dissolved. Then, 6 ml portions of the solution were injected into Bayer bottles and previously frozen at −40° C. in a feezer. The frozen solution was freeze-dried at a tray temperature of −5° C. for 20 hours with a freeze drier (manufactured by Labconco company, a stoppering tray drier). The temperature was raised to 30° C. to remove entirely the moisture remaining, and the freeze-dried material was dried in vacuo for 3 hours. After finishing the drying of the material, the bottles were capped in vacuo. 1.4 g of cosmetics were prepared by combining two ingredients, namely the above material and the following face lotion.

| [Composition of face lotion] | |
|---|---|
| Glycerin | 3.0% |
| Propylene glycol | 4.0% |
| Dipropylene glycol | 4.0% |
| Oleyl alcohol | 0.1% |
| Polyoxyethylene sorbitan monolauric ester | 1.5% |
| Ethyl alcohol | 15.0% |
| Purified water | 72.4% |
| Perfume | a little |

EXAMPLE 3

Preparation of the Cosmetic of this Invention

To 300 liters of a purified aqueous solution of 0.6 kg of sodium hyaluronate which was produced by a fermentation method (the concentration of sodium hyaluronate was 0.2%), 1.80 kg of magnesium-L-ascorbyl phosphate and 2.0 kg of mannitol were added with stirring and dissolved thoroughly. The obtained solution was placed in a glass vat so as to spread in a thickness of 1 cm and previously frozen at −60° C. in a freezer. The frozen material was freeze-dried for two days with a freeze drier (manufactured by Haru Japan Company, Pilot machine model type 2FS5). The freeze-dried material was powdered with a mill. The yield of the powdered material was 3.1 kg.

EXAMPLE 4

Preparation of the Cosmetic of this Invention

To 400 ml of purified water, 1.0 g of sodium hyaluronate was dissolved. To the obtained solution, 30.0 g of magnesium-L-ascorbyl phosphate was added and dissolved. Then, the solution was frozen in a freezer at −70° C. and the frozen solution was crushed with a freeze crusher (manufactured by Heiko Company, Type TI-500 DX). The crushed material was placed in a vat and freeze-dried. The freeze-dried material was granular and the yield was 21.0 g.

EXAMPLE 5

Results of Performance Test of the Cosmetic of this Invention

The cosmetic obtained in Example 1 was used. The cosmetic was dissolved in water on the palm of the hand and applied on the face skin.

As a comparative example, a mixture obtained by homogeneously mixing 33.3% of sodium hyaluronate and 66.7% of magnesium-L-ascorbyl phosphate was dissolved in water on the palm of the hand and applied on the face skin.

The feeling in applying on the skin and the solubility in water were tested by using the cosmetic of Example 1 and the cosmetic of the comparative example.

Feeling Test

About 5 mg of each sample was put on the palm of the hand, and about 0.3 ml of water was added and mixed by using the tip of a finger. The mixture was applied on the skin and the feeling was tested. The results are shown in Table 2.

TABLE 2

| | Feeling Test | |
|---|---|---|
| | Example 1 | Comparative Example |
| Feeling Test | o | x |

Judgement of the feeling test
When the mixture was applied on the skin,
o: people noted smooth feeling, and
x: people feel rough.

Solubility Test 50 ml of water was charged in a 100 ml beaker. Each sample of Table 3 was put in the beaker with stirring at a certain revolution by using a magnetic stirrer. The dissolving time of each sample in water was measured.

TABLE 3

| Sample | |
|---|---|
| Sample | Charge |
| a) Magnesium-L-ascorbyl phosphate | 0.10 |
| b) Sodium hyaluronate Molecular weight of 1,000,000 | 0.05 |
| c) Cosmetic of Comparative Example | 0.15 |
| d) Cosmetic of Example 1 | 0.15 |

The results are shown in Table 4.

TABLE 4

| | Solubility test result | | | |
|---|---|---|---|---|
| | a) | b) | c) | d) |
| Dissolving time (min.) | 20 | 28 | 28 | 12 |

The cosmetic of d) of the present invention, compared with the mixture product of c), has a good result. Namely, when the cosmetic was applied on the skin, people noted a smooth feeling. Further, the cosmetic dissolved in water in a short time compared with the mixture product and the compounds of a) and b).

EXAMPLE 6

Cosmetic Prepared by Using the Cosmetic of this Invention

Powder for Whitening

| Cosmetic obtained in Example 4 | 40.0% |
|---|---|
| 2,6-Ascorbic acid dipalmitate | 10.0% |
| D-Mannitol | 50.0% |

EXAMPLE 7

Lotion

| Cosmetic obtained in Example 4 | 3.1% |
|---|---|
| 1,3-butylene glycol | 8.0% |
| Glycerine | 4.0% |
| Methyl p-hydroxybenzoate | 0.1% |
| Polyoxyethylene-polyoxypropylene decyltetradecyl ether | 0.3% |
| Sodium citrate | 0.5% |
| Sodium edetate | 0.1% |
| Perfume | 0.1% |
| Purified water | 80.8% |

EXAMPLE 8

Beauty Liquid

| Cosmetic obtained in Example 4 | 3.1% |
|---|---|
| 1,3-butylene glycol | 8.0% |
| Glycerine | 4.0% |
| Xanthan gum | 0.3% |
| Sodium chondroitin sulfate | 0.1% |
| Ethanol | 3.0% |
| Methyl p-hydroxybenzoate | 0.1% |
| Polyoxyethylene-polyoxypropylene decyltetradecyl ether | 0.3% |
| Sodium citrate | 0.5% |
| Sodium edetate | 0.1% |
| Perfume | 0.1% |
| Purified water | 80.4% |

We claim:

1. A cosmetic comprising a freeze-dried material which is obtained by freeze-drying an aqueous solution containing hyaluronic acid or sodium hyaluronate and magnesium-L-ascorbyl phosphate.

2. A cosmetic as claimed in claim 1, wherein the freeze-dried product has a powder structure.

3. A cosmetic as claimed in claim 1 wherein the freeze-dried product has a granular structure.

4. A cosmetic as claimed in claim 1 wherein the ratio, by weight, of magnesium-L-ascorbyl phosphate: hyaluronic acid or sodium hyaluronate is 0.1 to 50:1.

5. A cosmetic as claimed in claim 1 wherein said cosmetic additionally includes at least one of a face paint, coloring agent, powder material, granular material, antioxidant, extender and perfume.

6. A cosmetic as claimed in claim 1 wherein said cosmetic additionally includes at least one of 2,6-ascorbic acid dipalmitate and D-mannitol.

7. A cosmetic as claimed in claim 1 wherein said cosmetic additionally includes at least one of 1,3-butylene glycol, glycerine, xanthan gum, sodium chondroitin sulfate, ethanol, methyl p-hydroxybenzoate, polyoxyethylene-polyoxypropylene, decyltetradecyl ether, sodium citrate, sodium edetate, perfume, and purified water.

* * * * *